United States Patent
Persson et al.

(10) Patent No.: US 6,710,219 B2
(45) Date of Patent: Mar. 23, 2004

(54) PANTY LINER

(75) Inventors: Charlotte Persson, Gothenburg (SE); Britt-Marie Wiezell, Molnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 78 days.

(21) Appl. No.: 10/102,659

(22) Filed: Mar. 22, 2002

(65) Prior Publication Data

US 2002/0193764 A1 Dec. 19, 2002

Related U.S. Application Data

(60) Provisional application No. 60/277,938, filed on Mar. 23, 2001.

(51) Int. Cl.$^7$ .................................................. A61F 13/15
(52) U.S. Cl. ........................................ 604/359; 604/367
(58) Field of Search ................................ 604/364, 367, 604/360, 359, 384

(56) References Cited

U.S. PATENT DOCUMENTS

| | | | | | |
|---|---|---|---|---|---|
| 3,804,094 | A | * | 4/1974 | Manoussos et al. | 604/359 |
| 5,641,503 | A | * | 6/1997 | Brown-Skrobot | 424/431 |
| 6,028,115 | A | * | 2/2000 | Zaneveld et al. | 514/709 |
| 6,080,908 | A | * | 6/2000 | Guarracino et al. | 604/359 |
| 6,180,100 | B1 | * | 1/2001 | Bruce et al. | 424/93.45 |
| 6,187,990 | B1 | * | 2/2001 | Runeman et al. | 604/360 |
| 6,203,810 | B1 | * | 3/2001 | Alemany et al. | 424/404 |
| 6,248,202 | B1 | * | 6/2001 | Corzani et al. | 156/270 |
| 6,359,191 | B1 | * | 3/2002 | Rusch et al. | 604/364 |
| 6,376,741 | B1 | * | 4/2002 | Guarracino et al. | 604/359 |
| 6,417,424 | B1 | * | 7/2002 | Bewick-Sonntag et al. | 604/367 |
| 6,417,427 | B1 | * | 7/2002 | Roxendal et al. | 604/378 |

FOREIGN PATENT DOCUMENTS

| | | | | |
|---|---|---|---|---|
| EP | 1118342 | * | 7/2001 | A61L/15/36 |
| JP | 61-275401 | | 12/1986 | |
| WO | WO 81/01643 | * | 6/1981 | A41B/13/02 |
| WO | WO 9945099 | * | 9/1999 | A61K/35/74 |

* cited by examiner

Primary Examiner—Weilun Lo
Assistant Examiner—Jacqueline F Stephens
(74) Attorney, Agent, or Firm—Young & Thompson

(57) ABSTRACT

A panty liner which includes active additives, such as lactobacilli. The liner includes a liquid-permeable top sheet which lies proximal to the wearer in use, a liquid-impermeable backing sheet which lies distal from the wearer in use, possibly an intermediate absorbent layer, and possibly fastener means. The panty liner is manufactured in a manner such that the active additives, preferably lactobacillus, are given a sufficiently effective and dry environment to ensure a healthy survival rate of the additives until the product is used.

13 Claims, No Drawings

PANTY LINER

This application claims benefit of provisional application No. 60/277,938, filed Mar. 23, 2001.

FIELD OF INVENTION

The present invention relates to panty liners that contain active additives, such as lactobacillus, and comprise a liquid-permeable top sheet which lies proximal to the wearer in use, a liquid-impermeable backing sheet which lies distal from the wearer in use and possibly an intermediate absorption layer and possibly also fastener means.

BACKGROUND OF THE INVENTION

In recent times, various types of active additives have begun to be used in absorbent products, such as diapers, panty liners and the like. Examples of such additives are deodorants such as zeolites and silica described in WO 97/46188, WO 97/46190, WO 97/46192, WO 97/46193, WO 97/46195 and WO 97/46196, for example. These additives are intended essentially to act in the product per se. Another example resides in the addition to diapers of softening additives, for example lotions, that are intended to be transferred from the product to the wearer's skin.

Active additives are intended to impart new or enhanced properties to the absorbent product in some respect. Lactic acid forming bacteria (lactobacillus) (mentioned in SE 9703669-3, SE 9502588-8, WO 92/13577, SE 9801951-6, SE 9804390-4, WO 00/01206 and WO 00/01207, among others), are applied to that part of the absorbent product which lies proximal to the wearer in use and are intended to be transferred to the wearer's genitals as a supplement to the wearer's own lactobacillus. This is particularly of value in situations where the own lactobacillus flora is weakened. For example, females of a fertile age naturally have lactobacillus in their genitals as a defence against undesired micro-organisms.

Since lactic acid forming bacteria (lactobacillus) are living organisms, and indeed must be alive in order to carry out their desired functions, it is important that the environment in which it such bacteria are present does not have a negative influence on their survival. This has been found problematic with regard to the development of products that include lactobacillus as an active component. It has been found that the survival of lactobacillus is negatively influenced primarily in a high humidity environment at room temperature. In order to ensure that the lactobacillus have a healthy storage environment, there has been developed a packaging unit which is sufficiently impervious to prevent the ingress of moisture during the storage period (WO 00/01207). The product is also subjected to a drying stage immediately prior to packaging the product, so as to ensure that the moisture content of the product will be sufficiently low when the package is sealed. This additional process step is, however, complicated and expensive. Consequently, there is a need for another production process or another lactobacillus-containing product that can provide for the lactobacillus a good and dry environment that is effective in ensuring healthy survival of the bacteria during storage.

The object of the present invention is to provide an absorbent article, primarily a panty liner, which enables the active additives to retain their activity prior to use of the product, without requiring further treatment, such as drying of the product to a greater or lesser extent.

SUMMARY OF THE INVENTION

This object is fulfilled with a panty liner that contains active additives, such as lactobacillus, and that comprises a liquid-permeable top sheet which lies proximal to the wearer in use, a liquid-impermeable backing sheet which lies distal from the wearer in use, optionally also an intermediate absorbent layer and optionally a fastener means, characterised in that the panty liner is produced chiefly from one or more low hygroscopic materials chosen from group of materials: non-woven, wadding, tow, and other synthetic fibre materials, wherein the moisture content of the panty liner is less than 2.5% after twenty-four hours at 22.5° C. in an humidity of 46%, preferably less than 2.0%, and more preferably less than 1.0%.

It has been found that under normal conditions such a panty liner will not absorb moisture to an extent that will have a negative effect on the healthy survival of the lactobacillus during storage. The panty liner may also include a superabsorbent for absorbing fluid that must, of necessity, be taken-up, such as menstruation fluid, this amount corresponding to 2–4 g fluid in normal cases. Thus, the superabsorbent material, which is applied in the core of the product, will take-up the fluid that must be taken-up in order for the product to fulfil its function in use. Although the remaining synthetic tow or wadding material has no appreciable hygroscopic capacity, it has a highly effective dry content at room temperature, which provides the lactobacillus with a dry environment during storage.

Paper based materials of different kinds are normally used in typical products of this kind. For example, pulp fibres, among other things, are most often used in the core of the article, because besides being hydrophilic, such fibres absorb moisture and liquid effectively and are inexpensive. By avoiding the use of paper fibres, as in the case of the present invention, there is achieved a lower moisture content in the product and therefore a higher survival rate of the lactobacillus. A sufficiently effective absorption capacity is obtained in the product with the use of superabsorbents that have the capacity of absorbing anticipated volumes of liquid discharged in use, i.e. a typical volume of about 0–4 ml. In this case, the liquid take-up is concentrated at the core and the remainder of the panty liner is made of material that does not tend to absorb moisture.

The superabsorbent material used may have the form of small SAP grains, large SAP grains, or SAF (superabsorbent fibres). The absorbency of the article with respect to body fluids will therewith be sufficient without having the capacity to take-up an unnecessarily large amount of atmospheric moisture.

According to one embodiment, the product contains no superabsorbent, which is functional in those cases where no fluid is expected to be absorbed in use. This particularly applies to those cases in which it is only desired to transfer the lactobacillus to the wearer in use.

The product may conveniently be provided with a breathable backing sheet, so that less perspiration will be produced when wearing the product, and so that the product will not take-up an unnecessarily large amount of moisture.

DETAILED DESCRIPTION OF THE INVENTION

By low hygroscopic material is meant material that is able to take-up atmospheric moisture in an amount sufficiently low to maintain a substantially dry environment under normal storage conditions, for example material such as tow, wadding and other synthetic fibre materials.

By tow is meant here a synthetic material consisting of long polypropylene fibres that have been bonded by transversal welds so as to hold the material together.

Wadding is a synthetic high loft material which, for instance, is needled by thin air, resin bonded, thermobonded, or bonded by carded or combed fibres. Wadding is available commercially from, e.g., Libertex.

The inventive panty liner is comprised of a liquid-permeable top sheet, a liquid-impermeable backing sheet, and optionally an intermediate absorbent body. The active additives, preferably lactobacilli are applied in the close proximity of the top sheet. In order to ensure that the lactobacilli will survive and retain their activity until the product is used, it is important in accordance with the inventive concept that the material from which the panty liner is made will attract as little moisture as possible. Trials have shown that a moisture content of 2.5 weight-% is an upper limit value beneath which survival of the lactobacilli is good. Consequently, an inventive panty liner is made of material which will absorb less moisture than said upper limit under tested conditions (see Example 1), such as wadding and-tow, for instance.

Superabsorbent (SAP) is preferably used in order to satisfy those absorption requirements that can arise in use. When a superabsorbent is used, it may also be beneficial to apply a dispersion layer beneath the top sheet, in order to ensure that the liquid delivered by the wearer is led to the superabsorbent material.

In one embodiment, the low hygroscopic material is tow.

In another embodiment, the low hygroscopic material is wadding.

In another embodiment, the top sheet and the wadding are joined together by punctiform bonds or by linear bonds that form a pattern. This is achieved by welding or by applying a high pressure at points, along short lines (dashes) or in some other pattern, wherewith the width of the points or lines in the pattern is about 1–7 mm. This results in a combination of larger and smaller capillaries that promote liquid absorption and transportation of liquid to lower layers.

In a further embodiment, the low hygroscopic material is thick non-woven, for example carded, spun-bonded, or a white or brown non-woven, "Evolon" having splittable fibres, with a weight per unit area of 80–140 g/m², available from Freudenburg, or microfibres.

The superabsorbent material used in the inventive panty liner may have the form of SAP grains, e.g. Hysorb C 7100 from BASF, acid SAP, or SAF fibres. The superabsorbent material is applied in an amount in which it is able to absorb 0–6 g liquid, preferably 2–4 g liquid. This requires an addition of 0.1–0.5 g superabsorbent.

In one embodiment, the panty liner contains no superabsorbent.

When conditioning the inventive panty liner over a period of twenty-four hours and at a temperature of 22.5° C. and a humidity of 46%, the panty liner will have a moisture content that is lower than 2.5%, preferably lower than 2.0%, and most preferably lower than 1.0%.

By active additive is meant a substance, an agent or a composition that is applied to the absorbent article during its manufacture and that is intended to change or improve the function of the article in some way or another. Examples of active additives are deodorisers such as zeolite and silica, softeners, such as lotions, lactobacillus for inhibiting the cultivation of other micro-organisms, and acids, such as lactic acid and citric acid, acid SAP, and partially neutralised SAP which is intended to lower the pH and thereby inhibit bacterial growth. The active additive may, for instance, be a micro-organism. According to one preferred embodiment of the invention, the active additive is an acid-producing micro-organism. According to a more preferred embodiment of the invention, the active additive is a lactobacillus and more preferably a lactobacillus of the strain Lactobacillus plantarum LB 931 (deposition No. (DSM): 11918).

When the active moisture-sensitive additive is lactobacillus, the additive can be applied in the form of a freeze-dried powder containing lactobacilli, or in the form of a suspension that contains lactobacilli. In this regard, it us suitable to keep the water content as low as possible or the concentration of lactobacilli as high as possible in the suspension, so as to avoid the addition of unnecessary water that must be later dried off. Lactobacilli will preferably be applied in an appropriate quantity of $10^4$–$10^{11}$, preferably $10^6$–$10^{10}$ CFU/product (CFU: Colony Forming Unit).

The liquid-permeable top sheet is comprised of a soft skin-friendly material. The top sheet may be comprised of a layer of different types of non-woven fibre material, or most beneficially of tow or wadding. Other materials that can be used are perforated plastic films, plastic nets, stitched, crocheted or woven textiles, and combinations and laminates of these types of materials. The plastic may be a thermoplastic, for instance polyethylene (PE). The non-woven material may consist of synthetic fibres, such as polyethylene (PE), polypropylene (PP), polyurethane (PU), a polyester, nylon or regenerated cellulose, or a mixture of different fibres. All materials that are used for liquid-permeable top sheets in the production of absorbent articles, such as sanitary napkins, panty liners or incontinence guards, can be used for the liquid-permeable-top sheet of the inventive article, and it will be understood that the aforesaid materials have only been given by way of example, provided that they have effective acquisition properties.

The liquid-impermeable backing sheet consists of a flexible material, preferably a thin film of polyethylene (PE), polypropylene (PP) or a polyester, although it may alternatively consist of a laminate of liquid-permeable material, such as non-woven, wadding or tow, and a liquid-impermeable material. All materials used in liquid-impervious backing sheets for absorbent articles may be used. The backing sheet may, beneficially, be air-permeable.

When using superabsorbents, it is normally necessary to include in the absorbent article a dispersion layer for leading the liquid to be absorbed from the top surface of the article to the superabsorbent polymers. These polymers are normally comprised of paper fibres (cellulose fluff), which is hydrophilic and has capillarity. According to the invention, the dispersion layer is conveniently comprised of synthetic fibre wadding, which is not hydrophilic and therefore does not absorb liquid to the same extent as cellulose fluff. Such a dispersion layer also includes capillaries for dispersing the liquid that is absorbed. Wadding includes relatively large capillaries or pores and when these capillaries or pores are, e.g., welded to a surface material, there are created smaller capillaries/pores that have a greater liquid retention capacity. The presence of a dispersion layer reduces the risk of discharged fluid running to and over the edge of the panty liner and therewith discolouring the panties or other garments of the wearer. It can be suitable to include a liquid acquisition layer (dispersion layer), even when the top sheet itself has good liquid acquisition properties.

With respect to packaging of the inventive panty liner, reference is made to packages and packaging methods disclosed in WO 00/01207.

The panty liner has a length of 60–260 mm. The absorption body has a widest width of 30–80 mm, preferably about 70 mm, and a smallest width at its rear end of 5–20 mm, preferably about 10 mm.

The panty liner is produced conventionally, for example in length-wise production in a one-path or four-path continuous production line.

A number of devices can be used to fasten the panty liner to the wearer's panties, such as tabs, flaps (wings), adhesive strings or friction surfaces. The panty liner will preferably include flaps or wings that can be folded around the edge of the wearer's panties and therewith fold the liner in place. The flaps, or wings, may be provided with adhesive strings that are covered with release paper in their packaged state, such release paper consisting of silicone-coated paper that functions to protect the adhesive strings against contaminating substances, such as dust, dirt and the like, and also prevents said strings from drying-out prior to use. Alternatively, it is conceivable to replace the adhesive strings with friction coatings or the like in the region of the absorbent body. Moreover, solely one flap may be provided with adhesive strings, although it is then necessary for the flaps to be dimensioned so that they will mutually overlap subsequent to being folded-in against the underside of the wearer's panties, or after having been folded around the edges of the panties. Fastener devices other than adhesive may be used to fasten the panty liner to the wearer's panties, e.g. hook devices of the touch-and-close fastener type capable of co-acting with the textile material from which the panties are made.

Although the invention is primarily concerned with a panty liner, it will be understood that the inventive concept also includes other absorbent articles in which active additives are used.

The invention will now be described by way of an example, although it will be understood that the example ahs no limiting effect on the scope of the invention.

EXAMPLE 1

The moisture uptake of a number of material combinations was examined by conditioning the tested material samples over a period of twenty-four hours and at a temperature of 22.5° C. and a humidity of 46% (Table 1). Two independent tests were carried out with each material sample. The commercially available product "Grace" (also called Libresse Air) was used as a reference. This product includes polypropylene non-woven surface material, 140 grams of thermo-bonded LDA (Low Density Air-laid), and a breathable backing sheet of microporous polyethylene. The tests showed that all of the materials chosen exhibited values beneath 2.5% moisture content (with respect to weight), with the exception of the chosen reference material.

| Sample | Sample content | Moisture content |
|---|---|---|
| 1 | NW** + tow material with 1 g large SAP grain | 0.65%; 0.76% |
| 2 | NW** + tow material with 1 g small SAP grains | 1.10%; 1.00% |
| 3 | NW** + tow material with SAF | 2.42%; 2.18% |

-continued

| Sample | Sample content | Moisture content |
|---|---|---|
| 4 | NW** + tow | 0.70%; 1.43% |
| 5 | NW* + surface material with wadding | 2.39%; 1.04% |
| 6 | Brown Evolon (thick non-woven) | 2.34%; 2.42% |
| 7 | Reference* – Libresse Air | 3.78%; 3.72% |

*NW is carded material Terpol (26 g/m$^2$) from Tenotex.
**NW is spun-bonded 20 g/m$^2$ from BBA NW.

Table 1. Moisture take-up test. Conditioning of the samples over twenty-four hours at 22.5° C. and 46% humidity. All panty liners in the table have a PE backing sheet. The percentage values are in weight-%.

What is claimed is:

1. A panty liner that includes active additives and which comprises a liquid-permeable top sheet that lies proximal to the wearer in use, a liquid-impermeable backing sheet that lies distal from the wearer in use, wherein the panty liner comprises one or more low hygroscopic materials chosen from the group consisting of wadding, tow, non-woven and synthetic fibre materials, wherein the moisture content of the panty liner is less than 2.5 weight-% after twenty-four hours at 22.5° C. and 46% humidity, and wherein the active additives include lactobacillus and a deodorizer that is one of zeolite and silica.

2. A panty liner according to claim 1, wherein the low hygroscopic material is tow.

3. A panty liner according to claim 1, wherein the low hygroscopic material is wadding.

4. A panty liner according to claim 1, wherein the low hygroscopic material is thick non-woven or is manufactured from splittable fibres or microfibres.

5. A panty liner according to claim 1, wherein the panty liner also includes a dispersion layer.

6. A panty liner according to claim 1, wherein the top sheet is patterned with wadding.

7. A panty liner according to claim 1, wherein the panty liner further includes a superabsorbent material that has a total absorption capacity of up to 6 ml liquid per panty liner.

8. A panty liner according to claim 7, wherein the superabsorbent material is in the form of super absorbent polymer grains or granules.

9. A panty liner according to claim 7, wherein the superabsorbent material has the form of superabsorbent fibre (SAF).

10. A panty liner according to claim 1 wherein the backing layer is comprised of a breathable material.

11. The panty liner of claim 1, wherein the lactobacillus is of the strain Lactobacillus plantarum LB 931 (DSM: 11918).

12. The panty liner of claim 1, wherein the moisture content is less than 2.0%.

13. The panty liner of claim 12, wherein the moisture content is less than 1.0%.

* * * * *